US006652466B2

United States Patent
Sugo et al.

(10) Patent No.: US 6,652,466 B2
(45) Date of Patent: Nov. 25, 2003

(54) BLOOD FLOW VOLUME MEASUREMENT METHOD AND VITAL SIGN MONITORING APPARATUS

(75) Inventors: Yoshihiro Sugo, Tokyo (JP); Mitsushi Hyogo, Tokyo (JP); Hideo Ozawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 10/084,309

(22) Filed: Feb. 28, 2002

(65) Prior Publication Data

US 2002/0151805 A1 Oct. 17, 2002

(30) Foreign Application Priority Data

Mar. 1, 2001 (JP) ...................................... P2001-057424

(51) Int. Cl.[7] .................................................. A61B 5/02
(52) U.S. Cl. ........................ 600/504; 600/485; 600/490
(58) Field of Search ................................. 600/481, 483, 600/485, 504, 505, 506, 507, 486, 490, 492, 493, 494, 495

(56) References Cited

U.S. PATENT DOCUMENTS 6,475,153 B1 * 11/2002 Khair et al. ................. 600/485

FOREIGN PATENT DOCUMENTS

JP          3028152          2/2000

OTHER PUBLICATIONS

Nicholas T. Kouchoukos, M.D., Louis C. Sheppard, B.S., and Donald A. McDonald, D.M., D.Sc. "Estimation of Stroke Volume in the Dog by a Pulse Contour Method", vol. XXVI, May 1970, p. 611–623.

* cited by examiner

Primary Examiner—Max F. Hindenburg
Assistant Examiner—Navin Natnithithadha
(74) Attorney, Agent, or Firm—Sughrue Mion, PLLC

(57) ABSTRACT

A vital sign monitoring apparatus has estimated blood pressure calculation device for calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, systolic and diastolic duration measurement device for successively measuring a systolic duration and a diastolic duration, and blood flow volume calculation device for calculating a blood flow volume based on the estimated systolic blood pressure and the estimated diastolic blood pressure successively calculated and the systolic duration and the diastolic duration successively measured.

35 Claims, 6 Drawing Sheets

BLOOD FLOW VOLUME MEASUREMENT METHOD AND VITAL SIGN MONITORING APPARATUS

BACKGROUND OF INVENTION

1. Field of Invention

This invention relates to a blood flow volume measurement method and a vital sign monitoring apparatus and in particular to a blood flow volume measurement method of measuring the blood flow volume ejected by cardiac contraction in vital sign monitoring apparatus and a vital sign monitoring apparatus.

2. Related Art

In medical facilities, variation in the hemodynamics of a patient in an operating room, an intensive care unit, an emergency treatment room, artificial dialysis treatment room, etc., needs to be monitored continuously as much as possible.

Hitherto, the variation in the hemodynamics of such a patient has been monitored mainly by monitoring the blood pressure directly.

In a living body, the cardiac output and the systemic vascular resistance are adjusted so that the blood pressure of the center is limited within a certain range. Therefore, to know the variation in the hemodynamics of a patient at an early stage, it is not enough to only monitor the blood pressure directly, and when change in the blood pressure is observed, the cause of the change in the blood pressure needs to be known. Then, in addition to change in the blood pressure, change in the cardiac output needs to be monitored.

As a method of measuring the change in the cardiac output to monitor the variation in the hemodynamics of a patient, methods are used as described below such as a thermo dilution method, a dye dilution method, and an ultrasound method.

First, the thermo dilution method will be discussed.

In the thermo dilution method a Swan-Ganz catheter is inserted through a jugular vein, a given amount of cooled saline or cooled glucose solution is poured to a central vein or a right atrial, and the cardiac output is measured from temperature change in a pulmonary artery.

Recently, another thermo dilution method of measuring the cardiac output from temperature change caused by blood warmed through a catheter has also been available; according to this method, the cardiac output can be measured automatically every given time.

Next, the dye dilution method will be discussed.

In the dye dilution method, a given amount of dye is poured through a vein, and the dye concentration is measured invasively or non-invasively in the part where the dye is uniformly diluted to a constant concentration, and the cardiac output is measured.

Next, the ultrasound method will be discussed.

The ultrasound method is a method of measuring the inner diameter of an arterial blood vessel such as a descending aorta and the blood flow velocity using ultrasound transesophageally, thereby the cardiac output is measured.

Aforementioned methods measuring cardiac output for monitoring the variation in the hemodynamics of a patient in the related arts involve the following problems:

The thermo dilution method involves a problem of intermittent measurement and incapability of continuous measurement. Inserting a catheter in the thermo dilution method is highly invasive for a patient and involves a possible danger of infection, etc.

Further, the thermo dilution method is a method requiring a skilled medical person for measurement and inserting a catheter.

Recently, a continuous measurement method has also been developed in the thermo dilution method, but the method requires insertion of a catheter and the above-described problem cannot be solved.

The dye dilution method also involves a problem of incapability of continuous measurement and requires a skilled medical person.

The ultrasound method imposes a burden of stress on a patient because a transducer is attached transesophageally.

Recently, a non-invasive measurement from the body surface has also been available as a kind of the ultrasound method, but continuous measurement is impossible.

Considering requirement for an advanced skill of medical person and an invasive procedure for a patient, the methods described above cannot continuously be conducted easily and it is difficult to monitor the variation in the hemodynamics of a patient continuously at all times by the methods.

SUMMARY OF THE INVENTION

It is therefore an object of the invention to provide a vital sign monitoring apparatus and a method of measuring the blood flow volume ejected by cardiac contraction in a vital sign monitoring apparatus capable of non-invensively monitoring the variation in the hemodynamics of a patient continuously at all times.

According to a first aspect of the present invention, there is provided a blood flow volume measurement method of measuring a blood flow volume ejected by cardiac contraction in a vital sign monitoring apparatus, the blood flow volume measurement method comprising the steps of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, successively measuring a systolic duration and a diastolic duration, and calculating a blood flow volume ejected by cardiac contraction based on the estimated systolic blood pressure and the estimated diastolic blood pressure successively calculated and the systolic duration and the diastolic duration successively measured.

Since the estimated systolic blood pressure and the estimated diastolic blood pressure are thus calculated from the information relevant to blood pressure measured (non-invensively) successively, the variation in the hemodynamics of a patient can be monitored non-invensively continuously at all times. Further, a skilled medical person for inserting a catheter, etc., is not required.

According to a second aspect of the present invention, there is provided a blood flow volume measurement method of measuring a blood flow volume ejected by cardiac contraction in a vital sign monitoring apparatus, the blood flow volume measurement method comprising the steps of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, calculating an estimated systolic duration and an estimated diastolic duration of an aorta from a systolic duration and a diastolic duration of a peripheral blood vessel successively measured based on the relationship between the systolic or diastolic duration in the aorta and the systolic or diastolic duration in the peripheral blood vessel, and calculating a blood flow volume ejected by cardiac contraction based on the estimated systolic blood pressure, the estimated diastolic blood pressure, the estimated systolic duration, and the estimated diastolic duration successively calculated.

The systolic or diastolic duration in the aorta is thus measured intermittently, whereby the estimated systolic blood pressure and the estimated diastolic blood pressure can be corrected, so that more accurate estimates can be provided.

According to a third aspect of the present invention, there is provided a blood flow volume measurement method of measuring a blood flow volume ejected by cardiac contraction in a vital sign monitoring apparatus, the blood flow volume measurement method comprising the first step of measuring a predetermined systolic pulse wave area in an aorta, measuring a systolic duration or a diastolic duration in the aorta, and measuring first blood flow volume based on the predetermined systolic pulse wave area and the systolic duration or the diastolic duration, the second step of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure at the same time as the first blood flow volume is measured, and further measuring a systolic duration and a diastolic duration, the third step of determining a predetermined coefficient in a predetermined relational expression so that blood flow volume calculated according to the predetermined relational expression from the estimated systolic blood pressure, the estimated diastolic blood pressure, the systolic duration, and the diastolic duration successively calculated at the second step matches the first blood flow volume measured at the first step, the fourth step of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, the fifth step of successively measuring a systolic duration and a diastolic duration, and the sixth step of calculating a blood flow volume based on the estimated systolic blood pressure and the estimated diastolic blood pressure successively calculated and the systolic duration and the diastolic duration successively measured according to the predetermined relational expression using the predetermined coefficient determined at the third step.

The systolic pulse wave area and the systolic duration or the diastolic duration in the aorta are thus measured intermittently, whereby the estimated systolic blood pressure and the estimated diastolic blood pressure can be corrected, so that furthermore accurate estimates can be provided.

The blood flow volume measurement method according to a fourth aspect of the present invention, the fifth step successively calculates an estimated systolic duration and an estimated diastolic duration of an aorta from a systolic duration and a diastolic duration of a peripheral blood vessel successively measured, based on the relationship between the systolic or diastolic duration in the aorta and the systolic or diastolic duration in the peripheral blood vessel.

Since the relationship between the systolic or diastolic duration in the aorta and the systolic or diastolic duration in the peripheral blood vessel is thus previously found, the values of the aorta can be successively estimated from the measurement values of the peripheral blood vessel successively measured.

The blood flow volume measurement method according to a fifth aspect of the present invention, the step of calculating the blood flow volume calculates the cardiac output per unit time using a heart rate or a pulse rate successively measured.

Thus, the cardiac output (CO) can be found based on the heart rate (HR) successively measured or can be found based on the pulse rate (PR) successively measured.

The blood flow volume measurement method according to a sixth aspect of the present invention, the relationship between information relevant to blood pressure and systolic blood pressure and the relationship between information relevant to blood pressure and diastolic blood pressure are determined by the information relevant to blood pressure measured at blood pressure measuring time with a cuff and the systolic blood pressure and the diastolic blood pressure measured by blood pressure measurement with the cuff.

Thus, the information relevant to blood pressure, the systolic blood pressure, and the diastolic blood pressure can be measured with the cuff at the same time.

The blood flow volume measurement method according to a seventh aspect of the present invention, the information relevant to blood pressure is a value relevant to pulse wave propagation measured using electrocardiogram measurement means and photoelectric pulse wave detection means attached to a periphery.

Since the information is thus measured using the electrocardiogram measurement means and the photoelectric pulse wave detection means attached to the periphery of a patient, it can be measured non-invensively and successively.

The blood flow volume measurement method according to an eighth aspect of the present invention, the systolic or diastolic duration in the aorta is measured from a pulse wave detected by cuff pulse wave detection means for blood pressure measurement, and that the systolic or diastolic duration in the peripheral blood vessel is measured from a pulse wave detected by photoelectric pulse wave detection means attached to a periphery.

Thus, the systolic or diastolic duration in the aorta is measured by the cuff pulse wave detection means and the systolic or diastolic duration in the peripheral blood vessel is measured by the photoelectric pulse wave detection means.

The blood flow volume measurement method according to a ninth aspect of the present invention, the predetermined systolic pulse wave area in the aorta is calculated from a pulse wave detected by cuff pulse wave detection means for blood pressure measurement.

Thus, the systolic pulse wave area is calculated from the pulse wave detected by the cuff pulse wave detection means.

The blood flow volume measurement method according to a tenth aspect of the present invention further comprises the step of calibrating the relationship between the estimated systolic blood pressure, the estimated diastolic blood pressure, the systolic duration, and the diastolic duration based on which the blood flow volume is calculated at the step of calculating the blood flow volume and the blood flow volume according to the blood flow volume measured by an apparatus for measuring blood flow volume that can be used for another calibration.

Since an apparatus for measuring the blood flow volume that can be used for another calibration is thus used, calibration accuracy is more improved.

The blood flow volume measurement method according to an eleventh aspect of the present invention, the information relevant to blood pressure is a pulse wave propagation time or a pulse wave propagation velocity.

Thus, the pulse wave propagation time or the pulse wave propagation velocity can be used as the information relevant to blood pressure.

According to a twelfth aspect of the present invention, there is provided a vital sign monitoring apparatus comprising estimated blood pressure calculation means for calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, systolic and diastolic duration measurement means for successively measuring a systolic duration and a diastolic duration, and blood flow volume calculation means for calculating a blood flow volume ejected by cardiac contraction based on the estimated systolic blood pressure and the estimated diastolic blood pressure successively calculated and the systolic duration and the diastolic duration successively measured.

According to the configuration, since the estimated systolic blood pressure and the estimated diastolic blood pressure are calculated from the information relevant to blood pressure measured (non-invensively) successively, the variation in the hemodynamics of a patient can be monitored non-invensively continuously at all times. Further, a skilled medical person for inserting a catheter, etc., is not required.

The vital sign monitoring apparatus according to a thirteenth aspect of the present invention further comprises input means for externally inputting values for calibrating the relationship between the estimated systolic blood pressure, the estimated diastolic blood pressure, the systolic duration, and the diastolic duration based on which the blood flow volume calculation means calculates the blood flow volume, and the blood flow volume.

According to the configuration, the calibration values can be input externally through the input means.

The vital sign monitoring apparatus according to a fourteenth aspect of the present invention further comprises alarm output means for outputting an alarm when the blood flow volume successively calculated by the blood flow volume calculation means changes beyond a predetermined threshold value.

According to the configuration, when the blood flow volume changes beyond the predetermined threshold value, an alarm can be output.

The vital sign monitoring apparatus according to a fifteenth aspect of the present invention, the alarm output means outputs the contents containing an instruction notifying to calibrate the relationship between the estimated systolic blood pressure, the estimated diastolic blood pressure, the systolic duration, and the diastolic duration based on which the blood flow volume calculation means calculates the blood flow volume, and the blood flow volume.

According to the configuration, a calibration instruction alarm can be output.

According to a sixteenth aspect of the present invention, there is provided a blood flow volume measurement method of measuring a blood flow volume ejected by cardiac contraction in a vital sign monitoring apparatus, the blood flow volume measurement method comprising the steps of, based on the relationship between blood pressures at different levels and information relevant to blood pressure, calculating estimated blood pressures at the different levels from the successively measured information relevant to blood pressure, successively measuring a systolic duration and a diastolic duration, and calculating a blood flow volume based on the estimated blood pressure successively calculated and the systolic duration and the diastolic duration successively measured.

Since the estimated blood pressures at the different levels are thus calculated from the successively (non-invensively) measured information relevant to blood pressure, the variation in the hemodynamics of a patient can be monitored non-invensively continuously at all times. Further, a skilled medical person for inserting a catheter, etc., is not required.

According to a seventeenth aspect of the present invention, there is provided a blood flow volume measurement method of measuring a blood flow volume ejected by cardiac contraction in a vital sign monitoring apparatus, the blood flow volume measurement method comprising the steps of, based on the relationship between blood pressures at different levels and information relevant to blood pressure, calculating estimated blood pressures at the different levels from the successively measured information relevant to blood pressure, calculating an estimated systolic duration and an estimated diastolic duration of an aorta from a systolic duration and a diastolic duration of a peripheral blood vessel successively measured based on the relationship between the systolic or diastolic duration in the aorta and the systolic or diastolic duration in the peripheral blood vessel, and calculating a blood flow volume based on the estimated systolic blood pressure, the estimated diastolic blood pressure, the systolic duration, and the diastolic duration successively calculated.

Thus, since the estimated blood pressures at the different levels are calculated from the successively (non-invensively) measured information relevant to blood pressure, and further the systolic or diastolic duration of the aorta is estimated from successively measured the systolic or diastolic duration of peripheral vessel based on the relationship between the systolic or diastolic duration of the aorta and the systolic or diastolic duration of peripheral vessel, more accurate calculation of blood flow volume can be provided.

According to an eighteenth aspect of the present invention, there is provided a blood flow volume measurement method of measuring a blood flow volume ejected by cardiac contraction in a vital sign monitoring apparatus, the blood flow volume measurement method comprising the first step of measuring a predetermined systolic pulse wave area in an aorta, measuring a systolic duration or a diastolic duration in the aorta, and measuring first blood flow volume based on the predetermined systolic pulse wave area and the systolic duration or the diastolic duration, the second step of, based on the relationship between blood pressures at different levels and information relevant to blood pressure, calculating estimated blood pressures at the different levels from the successively measured information relevant to blood pressure at the same time as the first blood flow volume is measured, and further measuring a systolic duration and a diastolic duration, the third step of determining a predetermined coefficient in a predetermined relational expression so that blood flow volume calculated according to the predetermined relational expression from the estimated systolic blood pressure, the estimated diastolic blood pressure, the systolic duration, and the diastolic duration successively calculated at the second step matches the first blood flow volume measured at the first step, the fourth step of calculating estimated systolic blood pressure and estimated diastolic blood pressure from information relevant to blood pressure successively measured based on the relationship between blood pressures at different levels and information relevant to blood pressure, the fifth step of successively measuring a systolic duration and a diastolic duration, and the sixth step of calculating a blood flow volume based on the estimated systolic blood pressure and the estimated diastolic blood pressure successively calculated and the systolic duration and the diastolic duration successively measured according to the predetermined relational expression using the predetermined coefficient determined at the third step.

The systolic pulse wave area and the systolic duration or the diastolic duration in the aorta are thus measured intermittently, whereby the estimated systolic blood pressure and the estimated diastolic blood pressure can be corrected, so that furthermore accurate estimates can be provided.

The blood flow volume measurement method according to an nineteenth aspect of the present invention, any two of systolic blood pressure, diastolic blood pressure, mean blood pressure, end systolic blood pressure, mean systolic blood pressure, or mean diastolic blood pressure are used as the blood pressures at the different levels.

Two of the blood pressures at the different levels, the difference between which has statistically good correlation with the blood flow volume ejected by cardiac contraction, can be used.

The blood flow volume measurement method according to a twenty aspect of the present invention, the information relevant to blood pressure is information relevant to pulse wave propagation time.

Thus, the information relevant to the pulse wave propagation time can be used as the information relevant to blood pressure.

DETAILED DESCRIPTION OF PREFERRED EMBODIMENTS

Referring now to the accompanying drawings, there are shown embodiments of a blood flow volume measurement method and a vital sign monitoring apparatus according to the invention.

Figure 1:
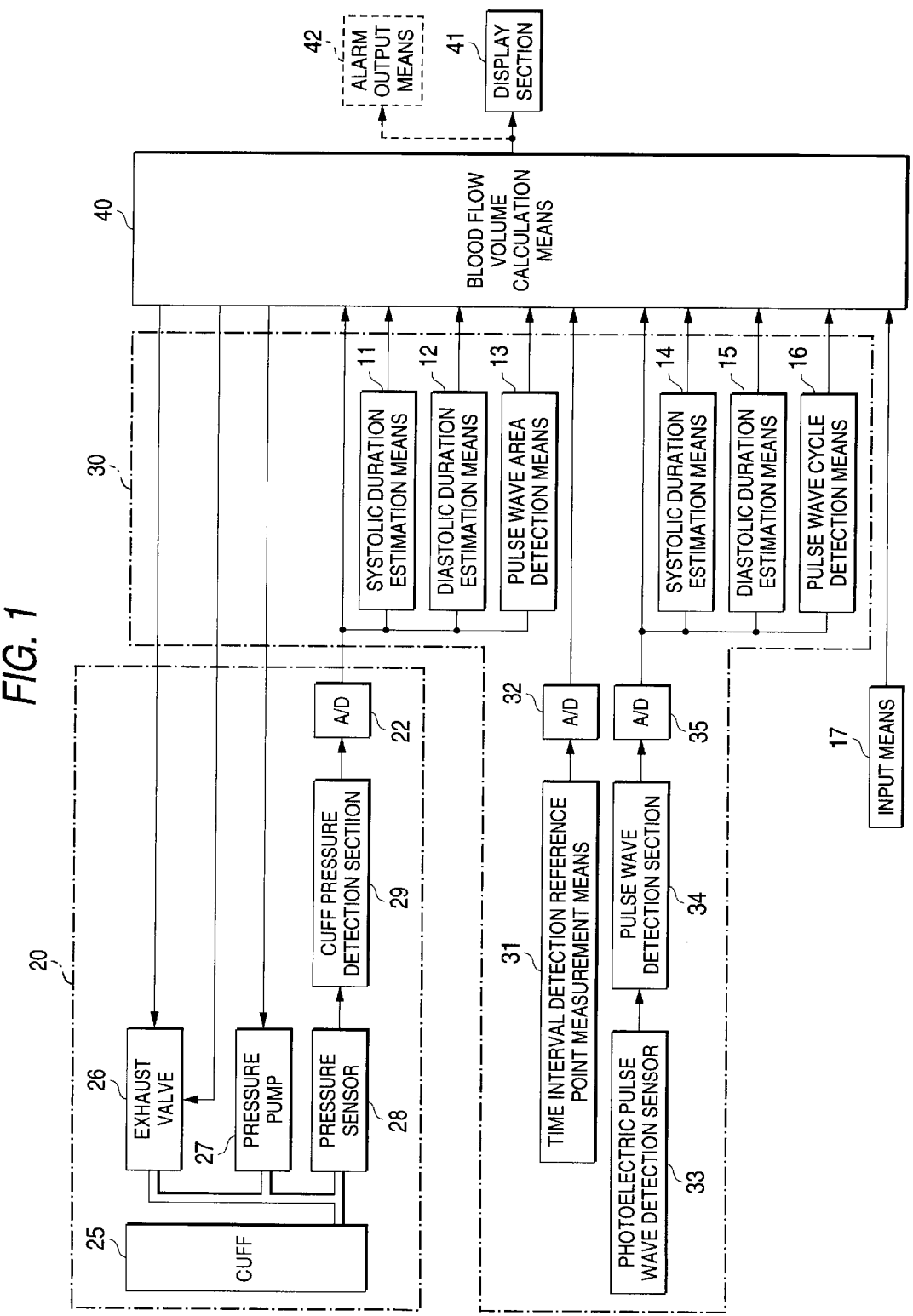
FIG. 1 is a block diagram to describe the configuration of one embodiment of a vital sign monitoring apparatus according to the invention.
Figure 2:
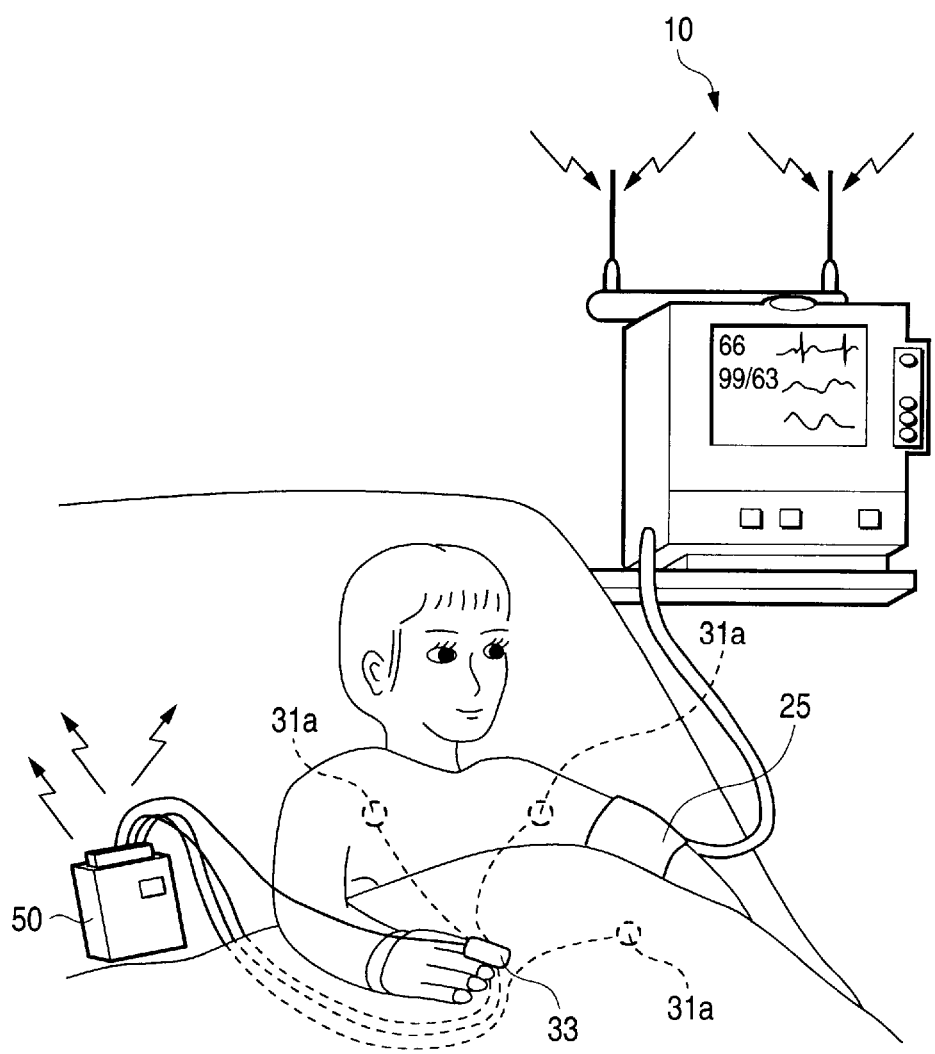
FIG. 2 is a schematic drawing to describe an example of a measurement mode of the vital sign monitoring apparatus according to the invention.
Figure 3:
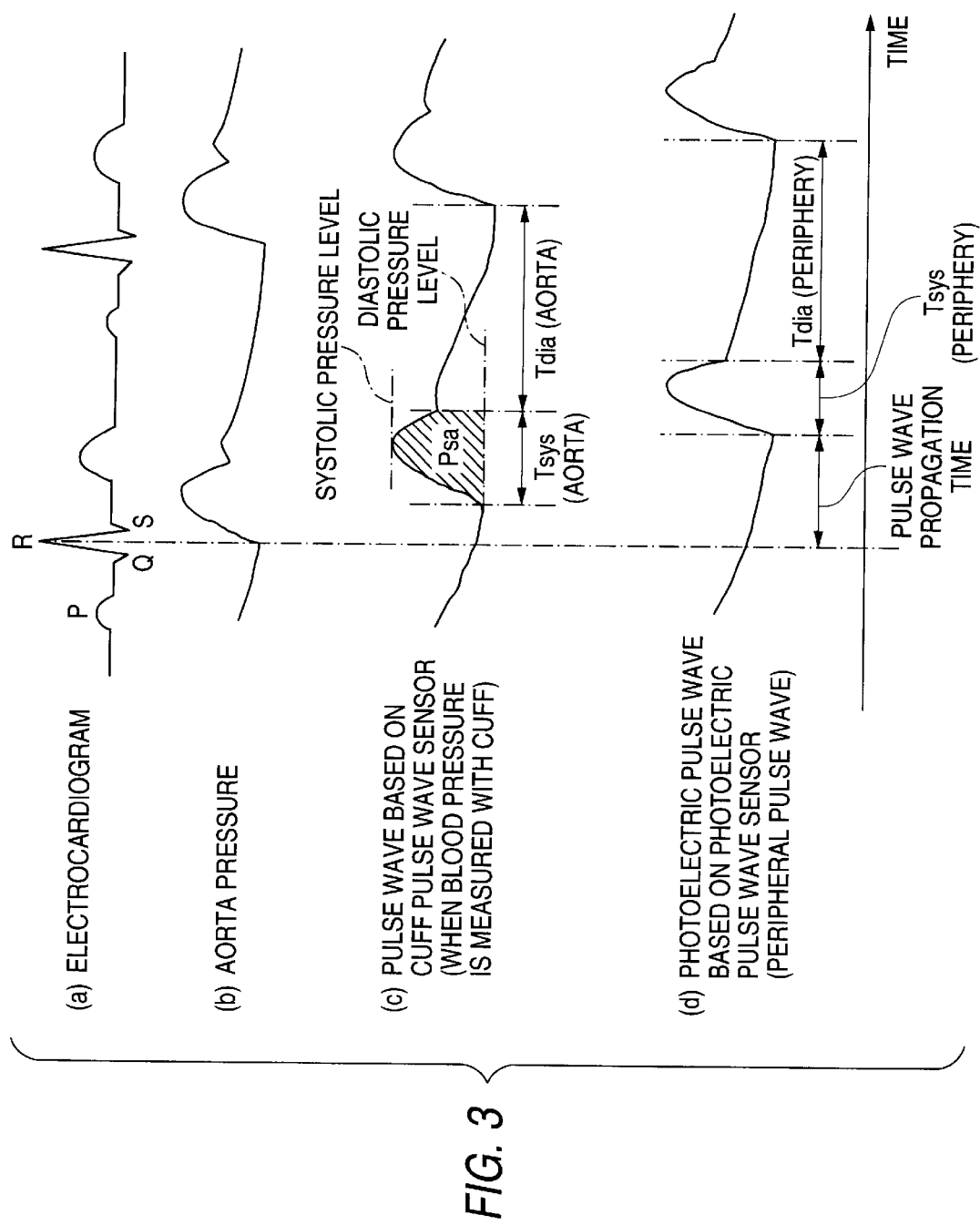
FIG. 3 is a chart to show waveforms of pulse waves measured by the vital sign monitoring apparatus according to the invention.

FIG. 1 is a block diagram to describe the configuration of one embodiment of a vital sign monitoring apparatus according to the invention, FIG. 2 is a schematic drawing to describe an example of a measurement mode of the vital sign monitoring apparatus according to the invention, and FIG. 3 is a chart to show waveforms of pulse waves measured.

Systolic and diastolic duration measurement means 20 for successively measuring the systolic duration and the diastolic duration is made up of a cuff 25, a pressure pump 27, a pressure sensor 28, a cuff pressure detection section 29, an A/D converter 22, etc., as shown in FIG. 1.

Specifically, the cuff 25 is attached to the brachial part of a patient for measurement, as shown in FIG. 2. The inside of the cuff 25 is opened to the atmosphere or is closed by an exhaust valve 26 placed in a vital sign monitoring apparatus main unit 10.

Air is supplied to the cuff 25 by the pressure pump 27 placed in the vital sign monitoring apparatus main unit 10. The pressure sensor 28 (cuff pulse wave sensor) is installed in the vital sign monitoring apparatus main unit 10 and output of the pressure sensor 28 is detected by the cuff pressure detection section 29. Output of the cuff pressure detection section 29 is converted into a digital signal by the A/D converter 22 and the digital signal is input to blood flow volume calculation means 40 (in FIG. 2, the cuff pressure detection section 29, the A/D converter 22, and the blood flow volume calculation means 40 are contained in the vital sign monitoring apparatus main unit 10).

The waveform of a pulse wave provided by the cuff pulse wave sensor as shown in FIG. 3(c) is thus provided.

The aorta pressure just after ejected from the heart becomes a waveform as shown in FIG. 3(b).

Estimated blood pressure calculation means 30 for calculating estimated systolic blood pressure Psys and estimated diastolic blood pressure Pdia from information relevant to blood pressure measured successively based on the relationship between information relevant to blood pressure and systolic blood pressure and the relationship between information relevant to blood pressure and diastolic blood pressure is made up of systolic duration estimation means 11, diastolic duration estimation means 12, and pulse wave area detection means 13 to which an output signal of the A/D converter 22 of the systolic and diastolic duration measurement means 20 is input, time interval detection reference point measurement means 31, and A/D converter 32, a photoelectric pulse wave detection sensor 33, a pulse wave detection section 34, an A/D converter 35, and systolic duration estimation means 14, diastolic duration estimation means 15, and pulse wave cycle detection means 16 to which an output signal of the A/D converter 35 is input, etc.

The time interval detection reference point measurement means 31 detects the point in time at which the aorta pressure reaches the bottom value almost at the same time as R wave of an electrocardiogram occurs, and output of the detection section is converted into a digital signal by the A/D converter 32 and the digital signal is input to the blood flow volume calculation means 40.

The time interval detection reference point measurement means 31 specifically is implemented as an ECG electrode 31a (electrocardiogram measurement means) attached to the breast of a subject, as shown in FIG. 2. Measurement data is wireless-transmitted from a measurement data transmitter 50 electrically connected to the ECG electrode 31a to the vital sign monitoring apparatus main unit 10. The transmitted measurement data is converted into a digital signal by the A/D converter 32 in the vital sign monitoring apparatus main unit 10 and the digital signal is input to the blood flow volume calculation means 40.

An electrocardiogram waveform as shown in FIG. 3(*a*) is thus provided.

In addition to the method of providing an electrocardiogram waveform from the ECG electrode 31*a* described above, a pulse wave provided from the heart sound heard when a microphone, etc., is put on the breast of a living body (phonocardiographic pulse wave) may be used.

On the other hand, the photoelectric pulse wave detection sensor 33 is attached to the periphery of a patient, such as his or her finger, as shown in FIG. 2 for providing information relevant to blood pressure (pulse wave propagation time, pulse wave propagation velocity, etc.,) by conducting $SPO_2$ measurement, etc., for example. The photoelectric pulse wave detection sensor 33 is electrically connected to the measurement data transmitter 50 for wireless-transmitting measurement data to the vital sign monitoring apparatus main unit 10. As the measurement data is sent to the pulse wave detection section 34 in the vital sign monitoring apparatus main unit 10, the pulse wave of the part of the patient to which the photoelectric pulse wave detection sensor 33 is attached (photoelectric pulse wave) is detected. Output of the pulse wave detection section 34 is converted into a digital signal by the A/D converter 35 and the digital signal is input to the blood flow volume calculation means 40.

The waveform of the photoelectric pulse wave (peripheral waveform) as shown in FIG. 3(*d*) is thus provided.

The ECG electrode 31*a* and the photoelectric pulse wave detection sensor 33 may be connected directly to the vital sign monitoring apparatus main unit 10 by wire without using the measurement data transmitter 50.

The processing result by the blood flow volume calculation means 40 is displayed on a display section 41 as text and image information.

Further, input means 17 is provided for externally inputting the values for calibrating the relationship between estimated systolic blood pressure Psys, estimated diastolic blood pressure Pdia, systolic duration Tsys, diastolic duration Tdia and blood flow volume. The blood flow volume calculation means 40 calculates blood flow volume based on this relationship.

The input means 17 may be any other than key input means; for example, a calibration value wire- or wireless-transmitted can also be received and be automatically input.

Alarm output means 42 may be provided for outputting an alarm when the blood flow volume successively calculated by the blood flow volume calculation means 40 changes beyond a predetermined threshold value.

The alarm output means 42 outputs the contents containing an instruction notifying to calibrate the relationship between the estimated systolic blood pressure Psys, the estimated diastolic blood pressure Pdia, the systolic duration Tsys, and the diastolic duration Tdia and the blood blow volume. The blood flow volume calculation means 40 calculates the blood flow volume based on this relationship.

Next, a method for measuring the blood flow volume ejected by cardiac contraction in the vital sign monitoring apparatus according to the invention will be discussed in detail with reference to the accompanying drawings as first to third embodiments.

The method in each embodiment is to measure the blood flow volume in the measurement mode as previously described with reference to FIG. 2, for example.

In blood pressure measurement with a cuff, preferably the pulse wave propagation time or velocity is measured in a time period over which the cuff pressure is reduced from average blood pressure to diastolic blood pressure. The reason is that when the arm to which the cuff 25 is attached and the hand (finger) to which the photoelectric pulse wave detection sensor 33 is attached are the same side, if the cuff pressure is high to the extent of the systolic pressure, the pulse wave does not propagate to the periphery or contains distortion.

However, such a problem does not arise if the arm to which the cuff 25 is attached and the hand (finger) to which the photoelectric pulse wave detection sensor 33 is attached are the different sides as shown in FIG. 2.

First Embodiment

Figure 4:
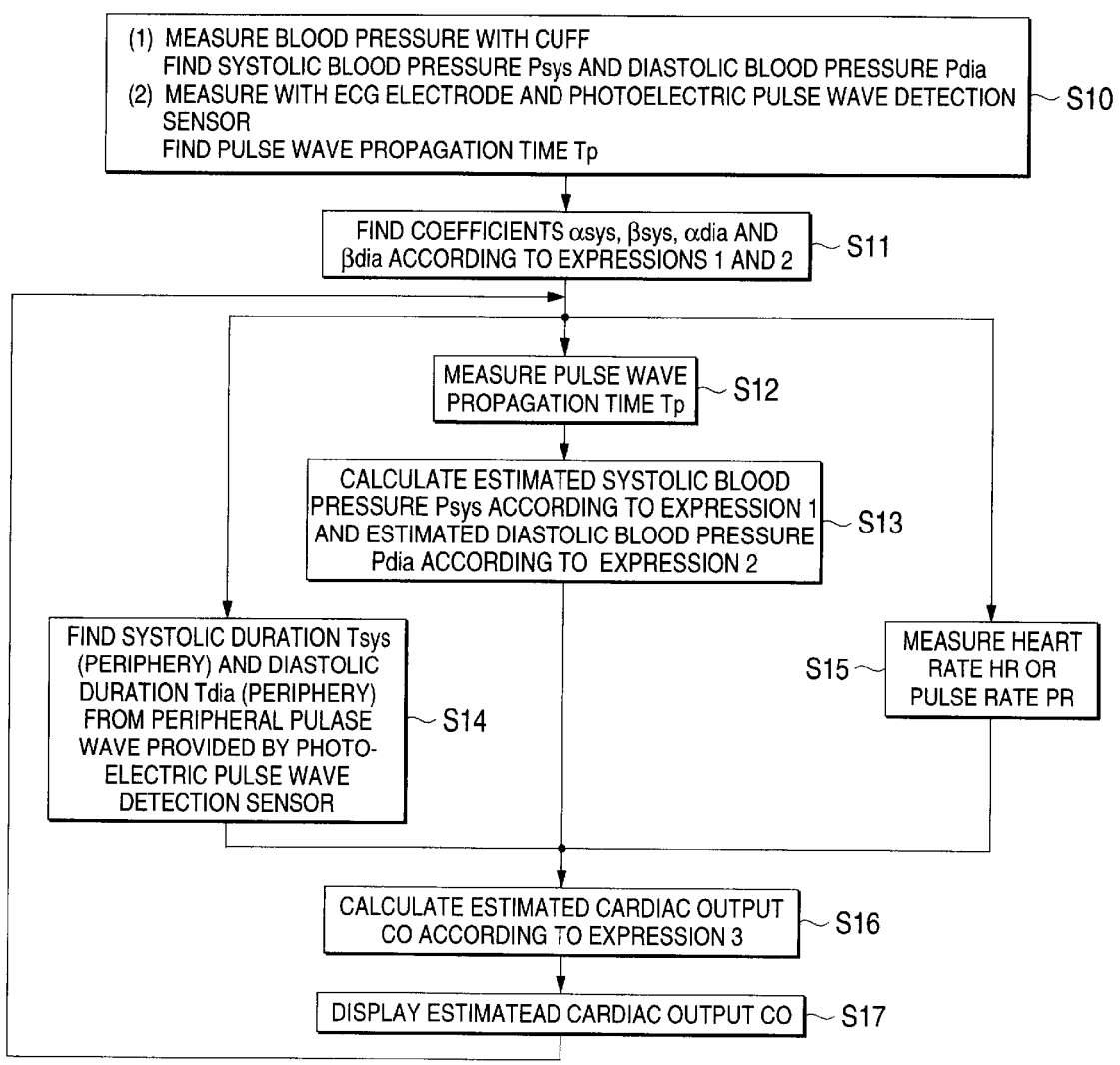
FIG. 4 is a flowchart to describe a first embodiment according to the invention.

FIG. 4 is a flowchart to describe a first embodiment according to the invention. Steps of the embodiment will be discussed with reference to FIG. 4. In the embodiment, measurement is conducted according to the flow shown in FIG. 4 in the measurement mode as previously described with reference to FIG. 2. FIG. 3 showing the waveforms of pulse waves measured is also referenced whenever necessary.

(Step S10)

(1) Blood pressure measurement with the cuff is conducted for finding systolic blood pressure and diastolic blood pressure.

(2) Measurement with the ECG electrode 31*a* and measurement with the photoelectric pulse wave detection sensor 33 are conducted at the same time as the blood pressure measurement with the cuff is conducted, and the pulse wave propagation time Tp is found from the time interval between the R wave of the electrocardiogram provided from the ECG electrode 31*a* (see FIG. 3(*a*)) and the bottom value of the photoelectric pulse wave (peripheral pulse wave) provided from the photoelectric pulse wave detection sensor 33 (see FIG. 3 (*d*)).

(Step S11)

The relation of P=αTp+β exists between the pulse wave propagation time Tp and the blood pressure P. The coefficients α and β are constants proper to each subject. If α and β are previously found, the blood pressure P can be estimated by calculation simply by measuring the pulse wave propagation time Tp obtained by the photoelectric pulse wave detection sensor 33 without conducting blood pressure measurement with the cuff.

Using the relation, at step S11, coefficients αsys, βsys, αdia, and βdia in the following Expressions 1 and 2, relational expressions between the systolic blood pressure Psys and the pulse wave propagation time Tp and the diastolic blood pressure Pdia and the pulse wave propagation time Tp are found by calculation:

$$Psys = \alpha sys \times Tp + \beta sys \qquad (1)$$

$$Pdia = \alpha dia \times Tp + \beta dia \qquad (2)$$

Measurement at step S10 is conducted at least twice, whereby the coefficients αsys, βsys, αdia, and βdia can be found by calculation.

To use a known value as either α or β, measurement at step S10 may be conducted only once; to use known values as both α and β, steps S10 and S11 may be skipped.

Next, steps S12 to S17 are successively executed for each pulse with the photoelectric pulse wave detection sensor 33 and the ECG electrode 31*a* attached to the subject. Alternatively, steps S12 to S17 may be executed every predetermined pulses and an average value may be found by calculation.

(Step S12)

The pulse wave propagation time Tp is found from the time interval between the R wave of the electrocardiogram waveform provided from the ECG electrode 31a (see FIG. 3(a)) and the bottom value of the photoelectric pulse wave (peripheral pulse wave) provided from the photoelectric pulse wave detection sensor 33 (see FIG. 3(d)).

(Step S13)

The value of the pulse wave propagation time Tp measured at step S12 is assigned to Expressions 1 and 2 and the estimated systolic blood pressure Psys and the estimated diastolic blood pressure Pdia are found by calculation.

(Step S14)

The peripheral systolic duration Tsys (periphery) and the diastolic duration Tdia (periphery) are found from the waveform of the photoelectric pulse wave (peripheral pulse wave) provided by the photoelectric pulse wave detection sensor 33 (see FIG. 3(d)).

(Step S15)

The number of times per minute, of the R wave of the electrocardiogram waveform provided from the ECG electrode 31a (see FIG. 3 (a)) is measured and heart rate HR is found. Alternatively, the number of times per minute, of the photoelectric pulse wave (peripheral pulse wave) provided from the photoelectric pulse wave detection sensor 33 (see FIG. 3(d)) is measured and pulse rate PR is found.

(Step S16)

The estimated cardiac output CO is found by calculation using the following expression 3 from the numeric values found at steps S12 to S15, Psys, Pdia, Tsys (periphery), Tdia (periphery), and HR or PR:

$$CO = K \times (estimated\ Psys - estimated\ Pdia) \times \\ Tsys\ (periphery) \times \left(1 + \frac{Tsys\ (periphery)}{Tdia\ (periphery)}\right) \times HR\ or\ PR \quad (3)$$

K is a constant and a numeric value statistically found based on clinical trial data is used or the cardiac output CO is found at the same time as or before step 10 by conducting the measurement method in the related art (thermo dilution method, dye dilution method, ultrasound method, etc.,) to a subject and a value calibrated so as to match the cardiac output CO is used. Alternatively, the value of K can also be input directly through the input means 17 from the outside.

(Step S17)

The estimated cardiac output CO calculated at step S16 is displayed on the display section 41. It may be displayed not only in a numeric value, but also in a graph form of trend display, etc.

Second Embodiment

Figure 5:
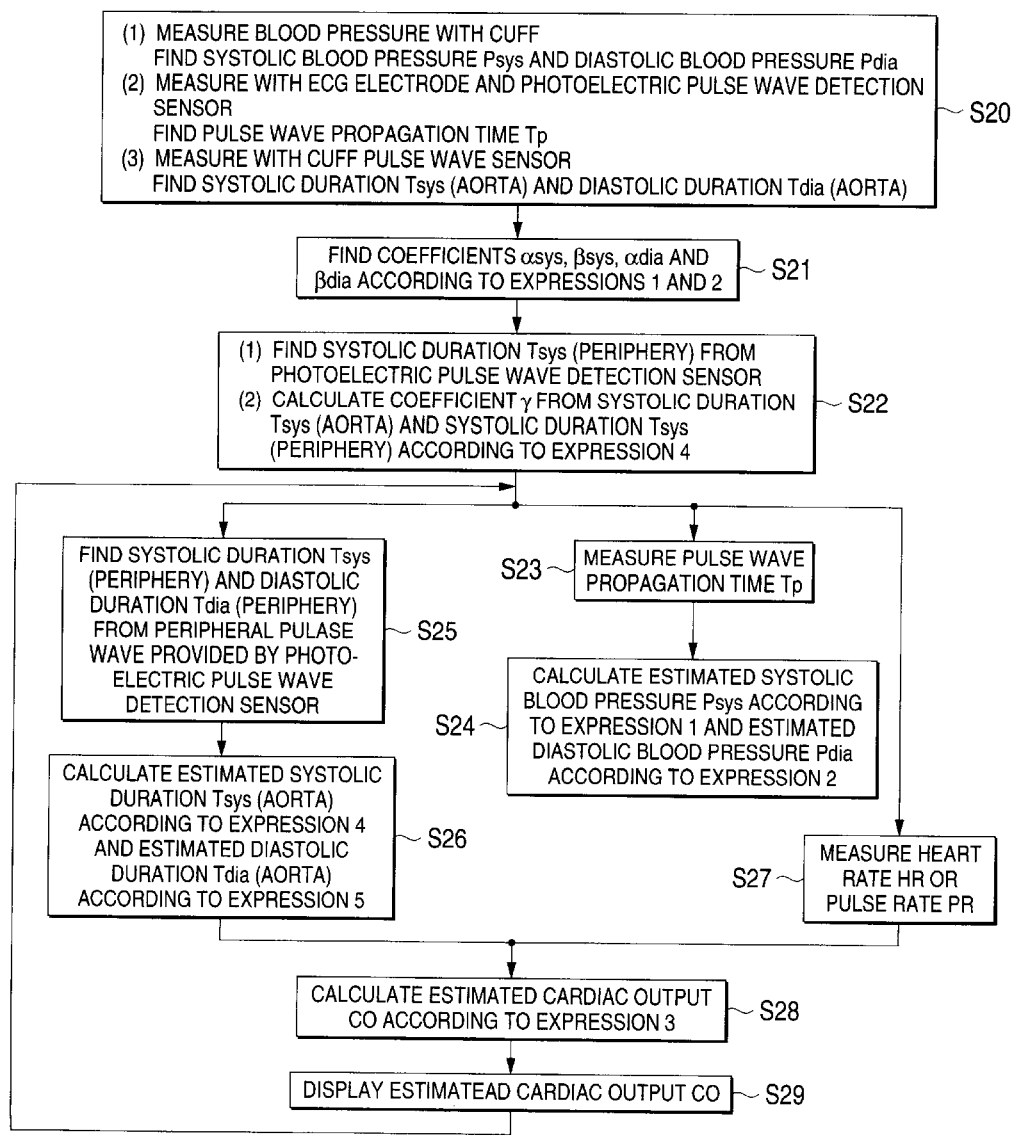
FIG. 5 is a flowchart to describe a second embodiment according to the invention.

FIG. 5 is a flowchart to describe a second embodiment of the invention. Steps of the embodiment will be discussed with reference to FIG. 5. In the embodiment, measurement is conducted according to the flow shown in FIG. 5 in the measurement mode as previously described with reference to FIG. 2. FIG. 3 showing the waveforms of measured pulse waves measured is also referenced whenever necessary.

(Step S20)

(1) Blood pressure measurement with the cuff is conducted for finding systolic blood pressure and diastolic blood pressure.

(2) Measurement with the ECG electrode 31a and measurement with the photoelectric pulse wave detection sensor 33 are conducted at the same time as the blood pressure measurement with the cuff is conducted in (1), and the pulse wave propagation time Tp is found from the time interval between the R wave of the electrocardiogram waveform provided from the ECG electrode 31a (see FIG. 3 (a)) and the bottom value of the photoelectric pulse wave (peripheral pulse wave) provided from the photoelectric pulse wave detection sensor 33 (see FIG. 3(d)).

(3) Measurement with the cuff pulse wave sensor is conducted at the same time as the measurement in (1), and the systolic duration Tsys (aorta) and the diastolic duration Tdia (aorta) are found (see FIG. 3(c)). A cuff waveform with the blood pressure equal to or less than the average blood pressure is used.

(Step S21)

The coefficients αsys, βsys, αdia, and βdia in (1) and (2) of the Expressions 1 and 2 described above are found by calculation as at step S11 of the first embodiment.

(Step S22)

The systolic duration Tsys (periphery) is found by measurement with the photoelectric pulse wave detection sensor 33 at step S20.

Difference value γ between the systolic duration Tsys (periphery) and the systolic duration Tsys (aorta) is found by calculation using the following Expression 4:

$$Systolic\ duration\ Tsys\ (aorta) = systolic\ dyrautib\ Tsys \\ (periphery) + \gamma \quad (4)$$

Next, steps S23 to S29 are successively executed for each pulse with the photoelectric pulse wave detection sensor 33 and the ECG electrode 31a attached to the subject. Alternatively, steps S23 to S29 may be executed every predetermined pulses and an average value may be found by calculation.

(Step S23)

The pulse wave propagation time Tp is found from the time interval between the R wave of the electrocardiogram waveform provided from the ECG electrode 31a (see FIG. 3(a)) and the bottom value of the photoelectric pulse wave (peripheral pulse wave) provided from the photoelectric pulse wave detection sensor 33 (see FIG. 3(d)).

(Step S24)

The value of the pulse wave propagation time Tp measured at step S23 is assigned to (1) and (2) of Expression 1 described above and the estimated systolic blood pressure Psys and the estimated diastolic blood pressure Pdia are found by calculation.

(Step S25)

The peripheral systolic duration Tsys (periphery) and the diastolic duration Tdia (periphery) are found from the waveform of the photoelectric pulse wave (peripheral pulse wave) provided by the photoelectric pulse wave detection sensor 33 (see FIG. 3(d)).

(Step S26)

Tsys (periphery) and γ are assigned to the Expression 3 described above and the estimated systolic duration Tsys (aorta) is found by calculation.

The estimated diastolic duration Tdia (aorta) is found by calculation using the following Expression 5:

$$Tdia\ (aorta) = [systolic\ duration\ Tsys\ (periphery) + \\ diastolic\ duration\ Tdia\ (periphery)] - \\ estimated\ systolic\ duration\ Tsys\ (aorta) \quad (5)$$

(Step S27)

The number of times per minute, of the R wave of the electrocardiogram waveform provided from the ECG electrode 31a (see FIG. 3(a)) is measured and heart rate HR is found. Alternatively, the number of times per minute, of the photoelectric pulse wave (peripheral pulse wave) provided from the photoelectric pulse wave detection sensor 33 (see FIG. 3(*d*)) is measured and pulse rate PR is found.

(Step S28)

The estimated cardiac output CO is found by calculation assigning the numeric values found at steps S23 to S27, Psys, Pdia, Tsys (aorta), Tdia (aorta), and HR or PR to the following Expression 6:

$$CO = K \times (estimated\ Psys - estimated\ Pdia) \times \qquad (6)$$
$$Tsys\ (aorta) \times \left(1 + \frac{Tsys\ (aorta)}{Tdia\ (aorta)}\right) \times HR\ or\ PR$$

K is a constant and a numeric value statistically found based on clinical trial data is used or the cardiac output CO is found at the same time as or before step 20 by conducting the measurement method in the related art (thermo dilution method, dye dilution method, ultrasound method, etc.,) to a subject and a value calibrated so as to match the cardiac output CO is used.

The value of K can also be input directly through the input means 17 from the outside.

(Step S29)

The estimated cardiac output CO calculated at step S28 is displayed on the display section 41. It may be displayed not only in a numeric value, but also in a graph form of trend display, etc.

Third Embodiment

Figure 6:
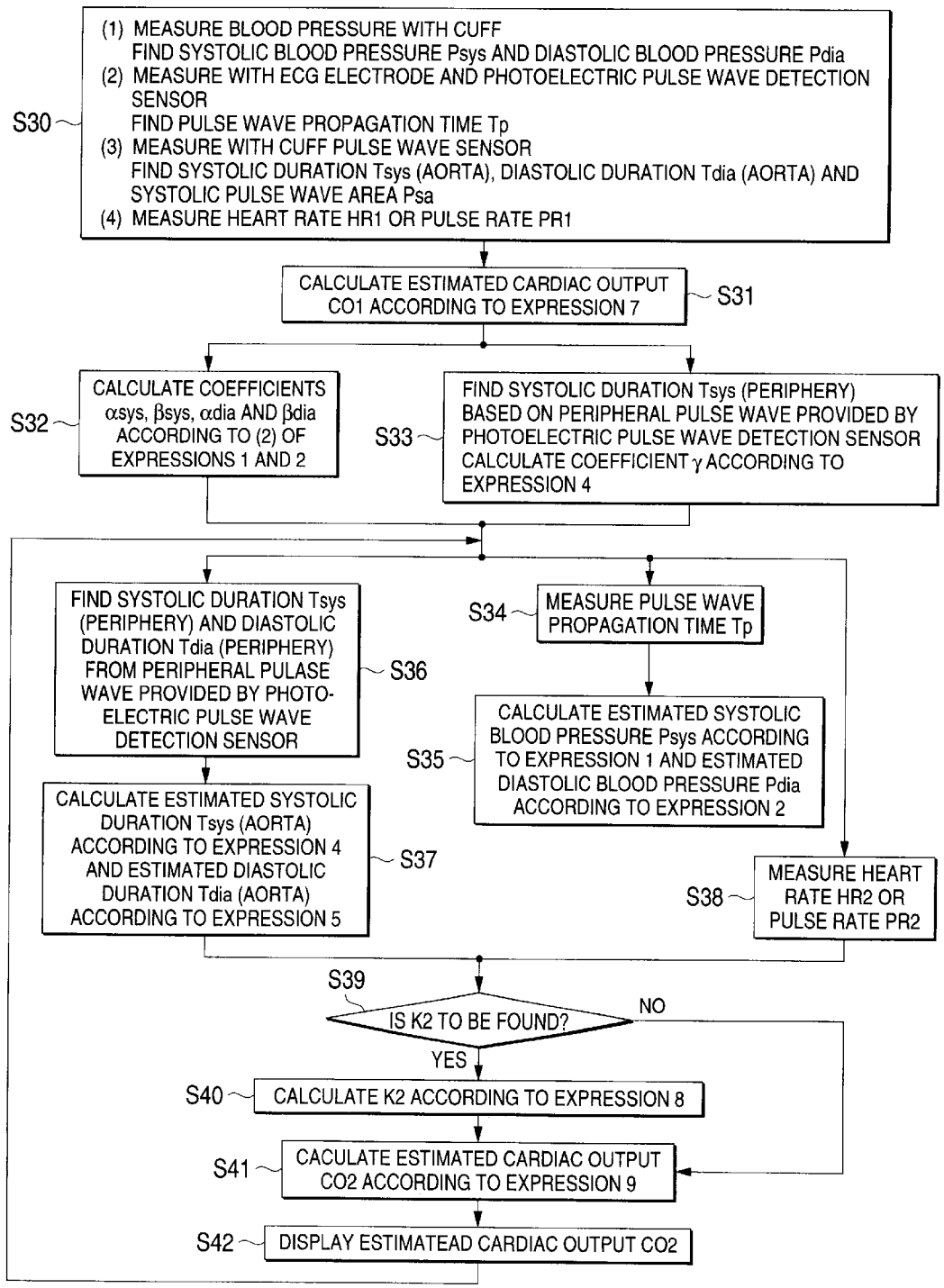
FIG. 6 is a flowchart to describe a third embodiment according to the invention.

FIG. 6 is a flowchart to describe a third embodiment of the invention. Steps of the embodiment will be discussed with reference to FIG. 6. In the embodiment, measurement is conducted according to the flow shown in FIG. 6 in the measurement mode as previously described with reference to FIG. 2. FIG. 3 showing the waveforms of measured pulse waves is also referenced whenever necessary.

(Step S30)

(1) Blood pressure measurement with the cuff is conducted for finding systolic blood pressure and diastolic blood pressure.

(2) Measurement with the ECG electrode 31*a* and measurement with the photoelectric pulse wave detection sensor 33 are conducted at the same time as the blood pressure measurement in (1) with the cuff is conducted, and the pulse wave propagation time Tp is found from the time interval between the R wave of the electrocardiogram waveform provided from the ECG electrode 31*a* (see FIG. 3(*a*)) and the bottom value of the photoelectric pulse wave (peripheral pulse wave) provided from the photoelectric pulse wave detection sensor 33 (see FIG. 3(*d*)).

(3) Measurement with the cuff pulse wave sensor is conducted at the same time as the measurement in (1), and the systolic duration Tsys (aorta), the diastolic duration Tdia (aorta), and systolic pulse wave area Psa are found (see FIG. 3(*c*)). The systolic pulse wave area Psa is the area between the diastolic blood pressure level and the systolic blood pressure level in the systolic duration Tsys (aorta), as shown in FIG. 3(*c*). In this measurement, cuff waveform with the blood pressure equal to or less than the average blood pressure is used.

(4) The number of times per minute, of the R wave of the electrocardiogram waveform provided from the ECG electrode 31*a* (see FIG. 3(*a*)) is measured and heart rate HR1 is found. Alternatively, the number of times per minute, of the photoelectric pulse wave (peripheral pulse wave) provided from the photoelectric pulse wave detection sensor 33 (see FIG. 3(*d*)) is measured and pulse rate PR1 is found.

(Step S31)

The numeric values found at step S30, Psa, Tsys (aorta), Tdia (aorta), and HR1 or PR1 are assigned to the following Expression 7 and estimated cardiac output CO1 is found by calculation:

$$CO1 = K1 \times Psa \times Tsys\ (aorta) \times \left(1 + \frac{Tsys\ (aorta)}{Tdia\ (aorta)}\right) \times HR1\ or\ PR1 \qquad (7)$$

K1 is a constant and a numeric value statistically found based on clinical trial data is used or the cardiac output CO1 is found at the same time as or before step 30 by conducting the measurement method in the related art (thermo dilution method, dye dilution method, ultrasound method, etc.,) to a subject and a value calibrated so as to match the cardiac output CO1 is used. Alternatively, the value of K1 can also be input directly through the input means 17 from the outside.

(Step S32)

The coefficients αsys, βsys, αdia, and βdia in the Expression 1 and 2 described above are found by calculation as at step S11 of the first embodiment.

(Step S33)

The systolic duration Tsys (periphery) is found by measurement with the photoelectric pulse wave detection sensor 33 at step S30.

Difference value γ between the systolic duration Tsys (periphery) and the systolic duration Tsys (aorta) is found by calculation according to the above-described Expression 4.

Next, steps S34 to S42 are successively executed for each pulse with the photoelectric pulse wave detection sensor 33 and the ECG electrode 31*a* attached to the subject. Alternatively, steps S34 to S42 may be executed every predetermined pulses and an average value may be found by calculation.

(Step S34)

The pulse wave propagation time Tp is found from the time interval between the R wave of the electrocardiogram waveform provided from the ECG electrode 31*a* (see FIG. 3(*a*)) and the bottom value of the photoelectric pulse wave (peripheral pulse wave) provided from the photoelectric pulse wave detection sensor 33 (see FIG. 3(*d*)).

(Step S35)

The value of the pulse wave propagation time Tp measured at step S30 is assigned to the Expressions 1 and 2 described above and the estimated systolic blood pressure Psys and the estimated diastolic blood pressure Pdia are found by calculation.

(Step S36)

The peripheral systolic duration Tsys (periphery) and the diastolic duration Tdia (periphery) are found from the waveform of the photoelectric pulse wave (peripheral pulse wave) provided by the photoelectric pulse wave detection sensor 33 (see FIG. 3(*d*)).

(Step S37)

Tsys (periphery) and γ are assigned to the Expression 4 described above and the estimated systolic duration Tsys (aorta) is found by calculation.

The estimated diastolic duration Tdia (aorta) is found by calculation according to the above-described Expression 5.

(Step S38)

The number of times per minute, of the R wave of the electrocardiogram waveform provided from the ECG electrode 31*a* (see FIG. 3(*a*)) is measured and heart rate HR2 is found. Alternatively, the number of times per minute, of the photoelectric pulse wave (peripheral pulse wave) provided from the photoelectric pulse wave detection sensor 33 (see FIG. 3(*d*)) is measured and pulse rate PR2 is found.

(Step S39)

Whether or not a coefficient K2 shown in Expression 9 described later is to be found is determined. If the coefficient K2 is to be found (Yes), control goes to step S40; if not found (No), control goes to step S41.

K2 is found if K2 is not yet determined or if the value of K2 is updated, etc.

(Step S40)

The estimated cardiac output CO1 found at step S31 as well as the numeric values found at steps S34 to S38, Psys, Pdia, Tsys (aorta), Tdia (aorta), and HR2 or PR2 is assigned to the following Expression 8 and K2 is found by calculation:

$$K2 = \frac{CO1}{(\text{estimated } Psys - \text{estimated } Pdia) \times Tsys \text{ (aorta)} \times} \quad (8)$$
$$\left(1 + \frac{Tsys \text{ (aorta)}}{Tdia \text{ (aorta)}}\right) \times HR \text{ or } PR$$

(Step 41)

K2, Psys, Pdia, Tsys (aorta), Tdia (aorta), and HR2 or PR2 are assigned to the following Expression 9 and estimated cardiac output CO2 is found by calculation:

$$CO2 = K2 \times \frac{(\text{estimated } Psys - \text{estimated } Pdia) \times Tsys \text{ (aorta)} \times}{\left(1 + \frac{Tsys \text{ (aorta)}}{Tdia \text{ (aorta)}}\right) \times HR \text{ or } PR} \quad (9)$$

(Step S42)

The estimated cardiac output CO2 found at step S41 is displayed on the display section 41. It may be displayed not only in a numeric value, but also in a graph form of trend display, etc.

In the described embodiments, the value of the pulse wave propagation time Tp may be found by measuring the time difference when the pulse wave appears between two different points, for example, the aorta and a peripheral blood vessel. A method of measuring the time difference based on a pulse wave (phonocardiographic pulse wave) provided from cardiac sound produced by putting a microphone, etc., on the chest of a living body may be used in addition to the above-described method of providing a pulse wave from the ECG electrode 31a.

In the described embodiments, the estimated blood pressure calculation means 30 may calculate estimates of mean blood pressure, end systolic blood pressure, mean systolic blood pressure, mean diastolic blood pressure in addition to measuring of systolic blood pressure and diastolic blood pressure or in place of either of the blood pressures.

For example, to adopt the mean blood pressure, the mean blood pressure can be found using the relation between Expressions 1 and 2 described above. That is, the relational expression of mean blood pressure Pmean can be found using the following Expression 10:

$$P\text{mean} = \alpha\text{mean} \times Tp + \beta\text{mean} \quad (10)$$

To adopt other blood pressures mentioned above, similar relational expressions are also set.

Thus, in addition to the systolic blood pressure and the diastolic blood pressure, the estimated blood pressures of the mean blood pressure, the end systolic blood pressure, the mean systolic blood pressure, and the mean diastolic blood pressure mentioned above can be used as the difference between blood pressures at different levels, the terms "(estimated Psys—estimated Pdia)" in each of Expressions 3, 6, 8 and 9.

If two of the estimated blood pressures, the difference between which has statistically good correlation with the blood flow volume ejected by cardiac contraction, are used to find the difference, a similar advantage to that of the gist of the invention can also be provided.

Further, in the described embodiments, a step of calibrating the relationship may be provided between the estimated systolic blood pressure, the estimated diastolic blood pressure, the systolic duration, and the diastolic duration based on which the blood flow volume is calculated and the blood flow volume according to the blood flow volume measured by an apparatus for measuring blood flow volume that can be used for another calibration.

The examples of such apparatus are a cardiac output meter based on a dye dilution method described in U.S. Pat. No. 3,028,152, a cardiac output meter based on a thermo dilution method, a cardiac output meter based on ultrasound measurement of artery area and blood flow velocity, etc.

As described above, according to the invention, the blood flow volume measurement method comprises the steps of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, successively measuring a systolic duration and a diastolic duration, and calculating a blood flow volume ejected by cardiac contraction based on the estimated systolic blood pressure and the estimated diastolic blood pressure successively calculated and the systolic duration and the diastolic duration successively measured. Accordingly, there can be provided the blood flow volume measurement method capable of monitoring the variation in the hemodynamics of a patient non-invasively continuously at all times, not requiring any skilled medical person for inserting a catheter, etc., and lessening the load on a patient.

According to the invention, the blood flow volume measurement method comprises the steps of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, calculating an estimated systolic duration and an estimated diastolic duration of an aorta from a systolic duration and a diastolic duration of a peripheral blood vessel successively measured based on the relationship between the systolic or diastolic duration in the aorta and the systolic or diastolic duration in the peripheral blood vessel, and calculating a blood flow volume ejected by cardiac contraction based on the estimated systolic blood pressure, the estimated diastolic blood pressure, the estimated systolic duration, and the estimated diastolic duration successively calculated. Accordingly, the estimated systolic blood pressure and the estimated diastolic blood pressure can be corrected, so that the blood flow volume measurement method capable of providing more accurate estimates can be provided.

According to the present invention, the blood flow volume measurement method comprises the first step of measuring a predetermined systolic pulse wave area in an aorta, measuring a systolic duration or a diastolic duration in the aorta, and measuring first blood flow volume based on the predetermined systolic pulse wave area and the systolic duration or the diastolic duration, the second step of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure at the same time as the first blood flow volume is measured, and further measuring a systolic duration and a diastolic duration, the third step of determining a predetermined coefficient in a predetermined relational expression so that blood flow volume calculated according to the predetermined relational expression from the estimated systolic blood pressure, the estimated diastolic blood pressure, the systolic duration, and the diastolic duration successively calculated at the second step matches the first blood flow volume measured at the first step, the fourth step of calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, the fifth step of successively measuring a systolic duration and a diastolic duration, and the sixth step of calculating a blood flow volume based on the estimated systolic blood pressure and the estimated diastolic blood pressure successively calculated and the systolic duration and the diastolic duration successively measured according to the predetermined relational expression using the predetermined coefficient determined at the third step. Accordingly, the estimated systolic blood pressure and the estimated diastolic blood pressure can be corrected, so that the blood flow volume measurement method capable of providing furthermore accurate estimates can be provided.

According to the present invention, the fifth step successively calculates an estimated systolic duration and an estimated diastolic duration of an aorta from a systolic duration and a diastolic duration of a peripheral blood vessel successively measured, based on the relationship between the systolic or diastolic duration in the aorta and the systolic or diastolic duration in the peripheral blood vessel. Accordingly, there can be provided the blood flow volume measurement method capable of successively estimating the values of the aorta from the measurement values of the peripheral blood vessel successively measured.

According to the present invention, the step of calculating the blood flow volume calculates the cardiac output per unit time using a heart rate or a pulse rate successively measured. Accordingly, there can be provided the blood flow volume measurement method capable of finding the cardiac output (CO) based on the heart rate (HR) successively measured or based on the pulse rate (PR) successively measured.

According to the present invention, the relationship between information relevant to blood pressure and systolic blood pressure and the relationship between information relevant to blood pressure and diastolic blood pressure are determined by the information relevant to blood pressure measured at blood pressure measuring time with a cuff and the systolic blood pressure and the diastolic blood pressure measured by blood pressure measurement with the cuff.

Accordingly, there can be provided the blood flow volume measurement method capable of measuring the information relevant to blood pressure, the systolic blood pressure, and the diastolic blood pressure using the cuff at the same time.

According to the present invention, the information relevant to blood pressure is a value relevant to pulse wave propagation measured using electrocardiogram measurement means and photoelectric pulse wave detection means attached to a periphery. Accordingly, the blood flow volume measurement method capable of measuring non-invensively and successively can be provided.

According to the present invention, the systolic or diastolic duration in the aorta is measured from a pulse wave detected by cuff pulse wave detection means for blood pressure measurement, and that the systolic or diastolic duration in the peripheral blood vessel is measured from a pulse wave detected by photoelectric pulse wave detection means attached to a periphery. Accordingly, there can be provided the blood flow volume measurement method capable of measuring the systolic or diastolic duration in the aorta by the cuff pulse wave detection means and the systolic or diastolic duration in the peripheral blood vessel by the photoelectric pulse wave detection means.

According to the present invention, the predetermined systolic pulse wave area in the aorta is calculated from a pulse wave detected by cuff pulse wave detection means for blood pressure measurement. Accordingly, there can be provided the blood flow volume measurement method capable of calculating the systolic pulse wave area from the pulse wave detected by the cuff pulse wave detection means.

According to the present invention, the blood flow volume measurement method further comprises the step of calibrating the relationship between the estimated systolic blood pressure, the estimated diastolic blood pressure, the systolic duration, and the diastolic duration based on which the blood flow volume is calculated at the step of calculating the blood flow volume and the blood flow volume according to the blood flow volume measured by an apparatus for measuring blood flow volume that can be used for another calibration. Accordingly, an apparatus for measuring the blood flow volume that can be used for another calibration is used, so that the blood flow volume measurement method capable of more improving the calibration accuracy can be provided.

According to the present invention, the information relevant to blood pressure is a pulse wave propagation time or a pulse wave propagation velocity. Accordingly, there can be provided the blood flow volume measurement method capable of using the pulse wave propagation time or the pulse wave propagation velocity as the information relevant to blood pressure.

According to the present invention, the vital sign monitoring apparatus comprises estimated blood pressure calculation means for calculating estimated systolic blood pressure and estimated diastolic blood pressure from information relevant to blood pressure successively measured based on the relationship between information relevant to blood pressure and systolic blood pressure and the relationship between information relevant to blood pressure and diastolic blood pressure, systolic and diastolic duration measurement means for successively measuring a systolic duration and a diastolic duration, and blood flow volume calculation means for calculating a blood flow volume ejected by cardiac contraction based on the estimated systolic blood pressure and the estimated diastolic blood pressure successively calculated and the systolic duration and the diastolic duration successively measured. Accordingly, since the estimated systolic blood pressure and the estimated diastolic blood pressure are calculated from the information relevant to blood pressure measured (non-invensively) successively, there can be provided the vital sign monitoring apparatus capable of monitoring the variation in the hemodynamics of a patient non-invensively continuously at all times and further not requiring any skilled medical person for inserting a catheter, etc.

According to the present invention, the vital sign monitoring apparatus further comprises input means for externally inputting values for calibrating the relationship between the estimated systolic blood pressure, the estimated diastolic blood pressure, the systolic duration, and the diastolic duration based on which the blood flow volume calculation means calculates the blood flow volume, and the blood flow volume, whereby there can be provided the vital sign monitoring apparatus to which calibration values measured in another apparatus, calibration values statistically calculated, etc., can be externally input.

According to the present invention, the vital sign monitoring apparatus further comprises alarm output means for outputting an alarm when the blood flow volume successively calculated by the blood flow volume calculation means changes beyond a predetermined threshold value, whereby there can be provided the vital sign monitoring apparatus capable of outputting an alarm when the blood flow volume changes beyond the predetermined threshold value, informing medical person of the fact.

According to the present invention, the alarm output means outputs the contents containing an instruction notifying to calibrate the relationship between the estimated systolic blood pressure, the estimated diastolic blood pressure, the systolic duration, and the diastolic duration based on which the blood flow volume calculation means calculates the blood flow volume, and the blood flow volume, whereby there can be provided the vital sign monitoring apparatus for enabling medical person to calibrate based on the instruction contents.

According to the present invention, the blood flow volume measurement method comprises the steps of, based on the relationship between blood pressures at different levels and information relevant to blood pressure, calculating estimated blood pressures at the different levels from the successively measured information relevant to blood pressure, successively measuring a systolic duration and a diastolic duration, and calculating a blood flow volume based on the estimated blood pressure successively calculated and the systolic duration and the diastolic duration successively measured. Accordingly, there can be provided the blood flow volume measurement method capable of monitoring the variation in the hemodynamics of a patient non-invensively continuously at all times, not requiring any skilled medical person for inserting a catheter, etc., and lessening the load on a patient.

According to the present invention, the blood flow volume measurement method comprises the steps of, based on the relationship between blood pressures at different levels and information relevant to blood pressure, calculating estimated blood pressures at the different levels from the successively measured information relevant to blood pressure, calculating an estimated systolic duration and an estimated diastolic duration of an aorta from a systolic duration and a diastolic duration of a peripheral blood vessel successively measured based on the relationship between the systolic or diastolic duration in the aorta and the systolic or diastolic duration in the peripheral blood vessel, and calculating a blood flow volume based on the estimated systolic blood pressure, the estimated diastolic blood pressure, the systolic duration, and the diastolic duration successively calculated. Accordingly, since the estimated blood pressures at the different levels are calculated from the successively (non-invasively) measured information relevant to blood pressure, and further the systolic or diastolic duration of the aorta is estimated from successively measured the systolic or diastolic duration of peripheral vessel based on the relationship between the systolic or diastolic duration of the aorta and the systolic or diastolic duration of peripheral vessel, more accurate calculation of blood flow volume can be provided.

According to the present invention, the blood flow volume measurement method comprises the first step of measuring a predetermined systolic pulse wave area in an aorta, measuring a systolic duration or a diastolic duration in the aorta, and measuring first blood flow volume based on the predetermined systolic pulse wave area and the systolic duration or the diastolic duration, the second step of, based on the relationship between blood pressures at different levels and information relevant to blood pressure, calculating estimated blood pressures at the different levels from the successively measured information relevant to blood pressure at the same time as the first blood flow volume is measured, and further measuring a systolic duration and a diastolic duration, the third step of determining a predetermined coefficient in a predetermined relational expression so that blood flow volume calculated according to the predetermined relational expression from the estimated systolic blood pressure, the estimated diastolic blood pressure, the systolic duration, and the diastolic duration successively calculated at the second step matches the first blood flow volume measured at the first step, the fourth step of calculating estimated systolic blood pressure and estimated diastolic blood pressure from information relevant to blood pressure successively measured based on the relationship between blood pressures at different levels and information relevant to blood pressure, the fifth step of successively measuring a systolic duration and a diastolic duration, and the sixth step of calculating a blood flow volume based on the estimated systolic blood pressure and the estimated diastolic blood pressure successively calculated and the systolic duration and the diastolic duration successively measured according to the predetermined relational expression using the predetermined coefficient determined at the third step. Accordingly, the estimated systolic blood pressure and the estimated diastolic blood pressure can be corrected, so that the blood flow volume measurement method capable of providing furthermore accurate estimates can be provided.

According to the present invention, any two of systolic blood pressure, diastolic blood pressure, mean blood pressure, end systolic blood pressure, mean systolic blood pressure, or mean diastolic blood pressure are used as the blood pressures at the different levels, whereby there can be provided the blood flow volume measurement method capable of using two of the blood pressures at the different levels, the difference between which has statistically good correlation with the blood flow volume ejected by cardiac contraction.

According to the present invention, the information relevant to blood pressure is information relevant to pulse wave propagation time, whereby there can be provided the blood flow volume measurement method capable of using the information relevant to the pulse wave propagation time as the information relevant to blood pressure.

What is claimed is:

1. A blood flow volume measurement method of measuring a blood flow volume ejected by cardiac contraction in a vital sign monitoring apparatus, said blood flow volume measurement method comprising the steps of:

calculating estimated systolic blood pressure and estimated diastolic blood pressure from information relevant to blood pressure measured based on the relationship between information relevant to blood pressure and systolic blood pressure and the relationship between information relevant to blood pressure and diastolic blood pressure;

measuring a systolic duration and a diastolic duration; and calculating a blood flow volume ejected by cardiac contraction based on the estimated systolic blood pressure and the estimated diastolic blood pressure calculated and the systolic duration and the diastolic duration measured.

2. The blood flow volume measurement method as claimed in claim 1, wherein said step of calculating the blood flow volume calculates the cardiac output per unit time using a heart rate or a pulse rate measured.

3. The blood flow volume measurement method as claimed in claim 1, wherein the relationship between information relevant to blood pressure and systolic blood pressure and the relationship between information relevant to blood pressure and diastolic blood pressure are determined by the information relevant to blood pressure measured at blood pressure measuring time with a cuff and the systolic blood pressure and the diastolic blood pressure measured by blood pressure measurement with the cuff.

4. The blood flow volume measurement method as claimed in claim 1, wherein the information relevant to blood pressure is a value relevant to pulse wave propagation measured using electrocardiogram measurement means and photoelectric pulse wave detection means attached to a periphery.

5. The blood flow volume measurement method as claimed in claim 1, further comprising: calibrating the relationship between the estimated systolic blood pressure, the estimated diastolic blood pressure, the systolic duration, and the diastolic duration based on which the blood flow volume is calculated at said step of calculating the blood flow volume and the blood flow volume according to the blood flow volume measured by an apparatus for measuring blood flow volume that can be used for another calibration.

6. The blood flow volume measurement method as claimed in claim 1, wherein the information relevant to blood pressure is a pulse wave propagation time or a pulse wave propagation velocity.

7. A blood flow volume measurement method of measuring a blood flow volume ejected by cardiac contraction in a vital sign monitoring apparatus, said blood flow volume measurement method comprising the steps of:

calculating estimated systolic blood pressure and estimated diastolic blood pressure from information relevant to blood pressure measured based on the relationship between information relevant to blood pressure and systolic blood pressure and the relationship between information relevant to blood pressure and diastolic blood pressure;

calculating an estimated systolic duration and an estimated diastolic duration of an aorta from a systolic duration and a diastolic duration of a peripheral blood vessel measured based on the relationship between the systolic or diastolic duration in the aorta and the systolic or diastolic duration in the peripheral blood vessel; and calculating a blood flow volume ejected by cardiac contraction based on the estimated systolic blood pressure, the estimated diastolic blood pressure, the estimated systolic duration, and the estimated diastolic duration calculated.

8. The blood flow volume measurement method as claimed in claim 7, wherein said step of calculating the blood flow volume calculates the cardiac output per unit time using a heart rate or a pulse rate measured.

9. The blood flow volume measurement method as claimed in claim 7, wherein the relationship between information relevant to blood pressure and systolic blood pressure and the relationship between information relevant to blood pressure and diastolic blood pressure are determined by the information relevant to blood pressure measured at blood pressure measuring time with a cuff and the systolic blood pressure and the diastolic blood pressure measured by blood pressure measurement with the cuff.

10. The blood flow volume measurement method as claimed in claim 7, wherein the information relevant to blood pressure is a value relevant to pulse wave propagation measured using electrocardiogram measurement means and photoelectric pulse wave detection means attached to a periphery.

11. The blood flow volume measurement method as claimed in claim 7, wherein the systolic or diastolic duration in the aorta is measured from a pulse wave detected by cuff pulse wave detection means for blood pressure measurement, and wherein the systolic or diastolic duration in the peripheral blood vessel is measured from a pulse wave detected by photoelectric pulse wave detection means attached to a periphery.

12. The blood flow volume measurement method as claimed in claim 7, further comprising: calibrating the relationship between the estimated systolic blood pressure, the estimated diastolic blood pressure, the systolic duration, and the diastolic duration based on which the blood flow volume is calculated at said step of calculating the blood flow volume and the blood flow volume according to the blood flow volume measured by an apparatus for measuring blood flow volume that can be used for another calibration.

13. The blood flow volume measurement method as claimed in claim 7, wherein the information relevant to blood pressure is a pulse wave propagation time or a pulse wave propagation velocity.

14. A blood flow volume measurement method of measuring a blood flow volume ejected by cardiac contraction in a vital sign monitoring apparatus, said blood flow volume measurement method comprising:

a first step for measuring a predetermined systolic pulse wave area in an aorta, measuring a systolic duration or a diastolic duration in the aorta, and measuring first blood flow volume based on the predetermined systolic pulse wave area and the systolic duration or the diastolic duration;

a second step for calculating estimated systolic blood pressure and estimated diastolic blood pressure from information relevant to blood pressure measured based on the relationship between information relevant to blood pressure and systolic blood pressure and the relationship between information relevant to blood pressure and diastolic blood pressure at the same time as the first blood flow volume is measured, and further measuring a systolic duration and a diastolic duration;

a third step for determining a predetermined coefficient in a predetermined relational expression so that blood flow volume calculated according to the predetermined relational expression from the estimated systolic blood pressure, the estimated diastolic blood pressure, the systolic duration, and the diastolic duration calculated at said second step matches the first blood flow volume measured at said first step;

a fourth step for calculating estimated systolic blood pressure and estimated diastolic blood pressure from information relevant to blood pressure measured based on the relationship between information relevant to blood pressure and systolic blood pressure and the relationship between information relevant to blood pressure and diastolic blood pressure;

a fifth step for measuring a systolic duration and a diastolic duration; and a sixth step for calculating a blood flow volume based on the estimated systolic blood pressure and the estimated diastolic blood pressure calculated and the systolic duration and the diastolic duration measured according to the predetermined relational expression using the predetermined coefficient determined at said third step.

15. The blood flow volume measurement method as claimed in claim 14, wherein said fifth step calculates an estimated systolic duration and an estimated diastolic duration of an aorta from a systolic duration and a diastolic duration of a peripheral blood vessel measured, based on the relationship between the systolic or diastolic duration in the aorta and the systolic or diastolic duration in the peripheral blood vessel.

16. The blood flow volume measurement method as claimed in claim 15, wherein the systolic or diastolic duration in the aorta is measured from a pulse wave detected by cuff pulse wave detection means for blood pressure measurement, and wherein the systolic or diastolic duration in the peripheral blood vessel is measured from a pulse wave detected by photoelectric pulse wave detection means attached to a periphery.

17. The blood flow volume measurement method as claimed in claim 14, wherein said step of calculating the blood flow volume calculates the cardiac output per unit time using a heart rate or a pulse rate measured.

18. The blood flow volume measurement method as claimed in claim 14, wherein the relationship between information relevant to blood pressure and systolic blood pressure and the relationship between information relevant to blood pressure and diastolic blood pressure are determined by the information relevant to blood pressure measured at blood pressure measuring time with a cuff and the systolic blood pressure and the diastolic blood pressure measured by blood pressure measurement with the cuff.

19. The blood flow volume measurement method as claimed in claim 14, wherein the information relevant to blood pressure is a value relevant to pulse wave propagation measured using electrocardiogram measurement means and photoelectric pulse wave detection means attached to a periphery.

20. The blood flow volume measurement method as claimed in claim 14, wherein the predetermined systolic pulse wave area in the aorta is calculated from a pulse wave detected by cuff pulse wave detection means for blood pressure measurement.

21. The blood flow volume measurement method as claimed in claim 14 further comprising: calibrating the relationship between the estimated systolic blood pressure, the estimated diastolic blood pressure, the systolic duration, and the diastolic duration based on which the blood flow volume is calculated at said step of calculating the blood flow volume and the blood flow volume according to the blood flow volume measured by an apparatus for measuring blood flow volume that can be used for another calibration.

22. The blood flow volume measurement method as claimed in claim 14, wherein the information relevant to blood pressure is a pulse wave propagation time or a pulse wave propagation velocity.

23. A vital sign monitoring apparatus comprising:

estimated blood pressure calculation means for calculating estimated systolic blood pressure and estimated diastolic blood pressure from information relevant to blood pressure measured based on the relationship between information relevant to blood pressure and systolic blood pressure and the relationship between information relevant to blood pressure and diastolic blood pressure;

systolic and diastolic duration measurement means for measuring a systolic duration and a diastolic duration; and blood flow volume calculation means for calculating a blood flow volume ejected by cardiac contraction based on the estimated systolic blood pressure and the estimated diastolic blood pressure calculated and the systolic duration and the diastolic duration measured.

24. The vital sign monitoring apparatus as claimed in claim 23 further comprising: input means for externally inputting values for calibrating the relationship between the estimated systolic blood pressure, the estimated diastolic blood pressure, the systolic duration, and the diastolic duration based on which said blood flow volume calculation means calculates the blood flow volume, and the blood flow volume.

25. The vital sign monitoring apparatus as claimed in claim 23 further comprising: alarm output means for outputting an alarm when the blood flow volume calculated by said blood flow volume calculation means changes beyond a predetermined threshold value.

26. The vital sign monitoring apparatus as claimed in claim 25 wherein the alarm output means outputs the contents containing an instruction notifying to calibrate the relationship between the estimated systolic blood pressure, the estimated diastolic blood pressure, the systolic duration, and the diastolic duration based on which said blood flow volume calculation means calculates the blood flow volume, and the blood flow volume.

27. A blood flow volume measurement method of measuring a blood flow volume ejected by cardiac contraction in a vital sign monitoring apparatus, said blood flow volume measurement method comprising the steps of:

calculating estimated blood pressures at the different levels from the measured information relevant to blood pressure on the basis of the relationship between blood pressures at different levels and information relevant to blood pressure;

measuring a systolic duration and a diastolic duration; and calculating a blood flow volume based on the estimated blood pressure calculated and the systolic duration and the diastolic duration measured.

28. The blood flow volume measurement method as claimed in claim 27, wherein any two of systolic blood pressure, diastolic blood pressure, mean blood pressure, end systolic blood pressure, mean systolic blood pressure, or mean diastolic blood pressure are used as the blood pressures at the different levels.

29. The blood flow volume measurement method as claimed in claim 27, wherein the information relevant to blood pressure is information relevant to pulse wave propagation time.

30. A blood flow volume measurement method of measuring a blood flow volume ejected by cardiac contraction in a vital sign monitoring apparatus, said blood flow volume measurement method comprising the steps of:

calculating estimated blood pressures at the different levels from the measured information relevant to blood pressure on the basis of the relationship between blood pressures at different levels and information relevant to blood pressure;

calculating an estimated systolic duration and an estimated diastolic duration of an aorta from a systolic duration and a diastolic duration of a peripheral blood vessel measured based on the relationship between the systolic or diastolic duration in the aorta and the systolic or diastolic duration in the peripheral blood vessel; and calculating a blood flow volume based on the estimated systolic blood pressure, the estimated diastolic blood pressure, the systolic duration, and the diastolic duration calculated.

31. The blood flow volume measurement method as claimed in claim 30, wherein any two of systolic blood pressure, diastolic blood pressure, mean blood pressure, end systolic blood pressure, mean systolic blood pressure, or mean diastolic blood pressure are used as the blood pressures at the different levels.

32. The blood flow volume measurement method as claimed in claim 30, wherein the information relevant to blood pressure is information relevant to pulse wave propagation time.

33. A blood flow volume measurement method of measuring a blood flow volume ejected by cardiac contraction in a vital sign monitoring apparatus, said blood flow volume measurement method comprising:

a first step for measuring a predetermined systolic pulse wave area in an aorta, measuring a systolic duration or a diastolic duration in the aorta, and measuring first blood flow volume based on the predetermined systolic pulse wave area and the systolic duration or the diastolic duration;

a second step, calculating estimated blood pressures at the different levels from the measured information relevant to blood pressure, based on the relationship between blood pressures at different levels and information relevant to blood pressure, at the same time as the first blood flow volume is measured, and further measuring a systolic duration and a diastolic duration;

a third step for determining a predetermined coefficient in a predetermined relational expression so that blood flow volume calculated according to the predetermined relational expression from the estimated systolic blood pressure, the estimated diastolic blood pressure, the systolic duration, and the diastolic duration calculated at said second step matches the first blood flow volume measured at said first step;

a fourth step for calculating estimated systolic blood pressure and estimated diastolic blood pressure from information relevant to blood pressure measured based on the relationship between blood pressures at different levels and information relevant to blood pressure;

a fifth step for measuring a systolic duration and a diastolic duration; and a sixth step for calculating a blood flow volume based on the estimated systolic blood pressure and the estimated diastolic blood pressure calculated and the systolic duration and the diastolic duration measured according to the predetermined relational expression using the predetermined coefficient determined at said third step.

34. The blood flow volume measurement method as claimed in claim 33, wherein any two of systolic blood pressure, diastolic blood pressure, mean blood pressure, end systolic blood pressure, mean systolic blood pressure, or mean diastolic blood pressure are used as the blood pressures at the different levels.

35. The blood flow volume measurement method as claimed in claim 33, wherein the information relevant to blood pressure is information relevant to pulse wave propagation time.

* * * * *